United States Patent [19]

Armenta

[11] Patent Number: 4,560,648
[45] Date of Patent: Dec. 24, 1985

[54] HOMOGENEOUS ENZYME IMMUNOASSAY FOR FERRITIN

[75] Inventor: Richard Armenta, Mountain View, Calif.

[73] Assignee: Syntex (U.S.A.) Inc., Palo Alto, Calif.

[21] Appl. No.: 535,014

[22] Filed: Sep. 23, 1983

[51] Int. Cl.$^4$ .................. G01N 53/00; G01N 33/549; C12N 9/96
[52] U.S. Cl. .......................... 435/7; 435/188; 435/810; 436/532; 436/801
[58] Field of Search .................. 435/7, 177, 188, 810; 436/801, 528, 532

[56] References Cited

U.S. PATENT DOCUMENTS

| | | | |
|---|---|---|---|
| 3,817,837 | 6/1974 | Rubenstein et al. | 435/7 |
| 4,150,033 | 5/1979 | Kitagawa | 435/7 X |
| 4,275,149 | 6/1981 | Litman et al. | 435/7 |
| 4,360,592 | 11/1982 | Weltman | 435/7 |
| 4,423,143 | 12/1983 | Rubenstein et al. | 435/188 X |

FOREIGN PATENT DOCUMENTS

| | | |
|---|---|---|
| 94777 | 11/1983 | European Pat. Off. |
| 2019562 | 10/1979 | United Kingdom |

OTHER PUBLICATIONS

Kitagawa et al., J. Biochem., 79, 233–236 (1976).
Theriault et al., Clin. Chem. 23/11:2142–2144 (1977).
Fortier et al., Clin. Chem. 25/8:1466–1469 (1979).
Conradie et al., S. Afr. Med. J., 57:282–287 (1980).
Page et al., Scand. J. Clin. Lab. Invest., 40:641–645 (1980).
Anderson et al., Clin. Chem. Acta., 116:405–408 (1981).
Linpisarn et al., Ann. Clin. Biochem., 18:48–53 (1981).

*Primary Examiner*—Christine M. Nucker
*Assistant Examiner*—Shawn P. Foley
*Attorney, Agent, or Firm*—Theodore J. Leitereg; Carole F. Barrett

[57] ABSTRACT

Composition and method are provided for enzyme immunoassays for high molecular weight proteins, such as ferritin. An enzyme is conjugated to the high molecular weight protein through a specific linking group. Usually, on the average, about 2 to 10 enzyme molecules are bonded to each protein molecule. In an assay, the conjugate competes with an unknown sample for receptor and the resulting enzymatic activity is compared to a standard for a determination of the presence and amount of protein in the unknown.

15 Claims, No Drawings

HOMOGENEOUS ENZYME IMMUNOASSAY FOR FERRITIN

BACKGROUND OF THE INVENTION

1. Field of the Invention

High molecular weight proteins have drawn increasing attention in recent years as knowledge of their functions and their significance in medical diagnoses has grown. One such protein is ferritin, which is the main form of stored iron in tissue. The liver is the most important site in which this form of iron is found. Also, in some pathological conditions such as overload of iron by blood transfusions, inflammation, and certain tumors, changes in the ferritin content of tissues are found. Measurement of serum ferritin reflects the amount of total iron stored in the body.

The need for sensitive and efficient assays for high molecular weight proteins such as ferritin has grown. To this end, various immunoassay techniques have been applied. The large size of these proteins, however, has heretofore limited the number of immunoassays which could provide a detectable signal. In particular, enzyme immunoassays have been limited to cumbersome procedures involving progressive binding reactions and phase separation. This is a serious limitation since enzyme immunoassays have the advantage of permitting spectrophotometric determinations and the potential of offering high sensitivity due to rapid substrate turnover rates which amplify the signal. A sensitive enzyme immunoassay is therefore needed which will permit the determination of large proteins in a simple and efficient manner.

2. Description of the Prior Art

Solid phase sandwich enzyme immunoassays for ferritin, a protein with a molecular weight of aproximately 450,000 daltons, are disclosed in Theriault et al., *Clin. Chem.*, 23/11:2142–2144 (1977); Fortier et al., *Clin. Chem.*, 25/8:1466–1469 (1979); Conradie et al., *S. Afr. Med. J.*, 57:282–287 (1980); Page et al., *Scand. J. Clin. Lab. Invest.*, 40:641–645 (1980); Anderson et al., *Clin. Chim. Acta.*, 116:405–408 (1981); and Linpisarn et al., *Ann. Clin. Biochem.*, 18:48–53 (1981).

Immunoassays for ferritin which do not involve enzymes include two-site immunoradiometric assays as disclosed in Addison et al., *J. Clin. Path.*, 25:326–329 (1972) and Miles et al., *Anal. Biochem.*, 61:209–224 (1974), competitive radioimmunoassays as disclosed in Porter, *J. Lab. Clin. Med.*, 83:147–152 (1974) and electroimmunoassays as disclosed in Carmel et al., *Anal. Biochem.*, 85:499–505 (1978) and Laurell, *Anal. Biochem.*, 15:45–52 (1966).

Enzyme coupled immunoassay of insulin using m-maleimidobenzoyl N-hydroxysuccinimide ester to conjugate β-D-galactosidase with insulin was described by Kitagawa et al., *J. Biochem.*, 79:233–236 (1976). Bifunctional reagents for cross-linking various proteins are disclosed in Wold, *Methods Enzymol.*, 25:623–651 (1972). Yoshitake et al., *J. Biochem.*, 101:395–399 (1979) discussed conjugation of glucose oxidase and rabbit antibodies using the N-hydroxysuccinimide ester of N-(4-carboxycyclohexylmethyl)maleimide and also conjugation of antigens and antibodies with β-galactosidase employing o-phenylenedimaleimide [N,N'-(1,2-phenylene)-bismaleimide]. Copending application U.S. Ser. No. 258,848 filed Apr. 29, 1981, now issued U.S. Pat. No. 4,423,143, discloses ligand-β-D-galactosidase conjugates for enzyme immunoassays.

SUMMARY OF THE INVENTION

Conjugates of high molecular weight proteins, such as ferritin, and an enzyme having available thiol groups, such as β-galactosidase, are provided for use in homogeneous enzyme immunoassays to provide high sensitivity in detecting extremely small amounts of the proteins. The high molecular weight protein is coupled to a bifunctional radical wherein one of the functionalities is reactive to amino groups on the protein. The other functionality is an activated olefin for coupling to the thiol groups of the enzyme. The functionalities are separated by a saturated alicyclic linking group having a cycloalkyl portion of from 5 to 7 carbon atoms and an alkylene portion of from 0 to 4 carbon atoms. The protein and enzyme molecules are linked in a proportion which, while permitting the retention of a substantial portion of the original enzyme activity of the enzyme with a macrosubstrate, causes a detectable reduction in such activity to occur upon the binding of a macromolecular receptor to the ferritin. The above conjugate may be used in homogeneous protein-binding assays for ferritin. The linking group employed in the present conjugate enables the required number of enzyme molecules to be bound to the high molecular weight protein so that an adequate change in signal, over the concentration range of interest, is achieved for purposes of an immunoassay.

DESCRIPTION OF THE SPECIFIC EMBODIMENTS

The present invention resides in conjugates of high molecular weight proteins, such as ferritin, through a specific linking group to an enzyme having available thiol groups, either native thiol groups or thiol groups introducted into the enzyme according to known procedures, such as β-galactosidase. A plurality of enzyme molecules is bonded to a single protein molecule (ligand). The number of enzyme molecules is limited, however, to permit macrosubstrate contact with the enzyme molecules to an extent sufficient to allow the enzyme to act upon the macrosubstrate thus producing a detectable signal. In addition, the protein in each conjugate has at least one epitopic site acessible for ligand-receptor binding with sufficient enzyme proximity to result in a measurable degree of enzyme inhibition upon binding of the receptor to the ligand. The conjugates are useful in homogeneous protein-binding assays for detection of the protein in an unknown sample. In the assay, the conjugate and the analyte compete for a limited amount of receptor in a homogeneous mixture. To the extent that the unknown sample contains the analyte protein, the amount of receptor available for binding to the protein in the conjugate is reduced. The mixture is then analyzed for enzymatic activity. A change in enzymatic activity over that in the absence of the analyte indicates the presence of analyte in the unknown sample.

The term "analyte" refers to a compound or composition to be measured, normally a ligand which is mono- or polyepitopic and usually antigenic.

The term "ligand" when used herein means a high molecular weight protein capable of conjugation to an enzyme in accordance with the present invention.

The term "receptor" means any compound or composition capable of recognizing a particular spatial and polar organization of a ligand, usually an antibody.

The compounds of the invention will normally have the following formula:

  (I)

wherein:

F is a protein of molecular weight of from about 250,000–1,000,000 daltons, preferably between about 400,000 and about 600,000 daltons;

m is 0 or 1;

R is a saturated alicyclic linking group having a cycloalkyl portion of from 5 to 7 carbon atoms and an alkylene portion of from 0 to 4 carbon atoms, preferably 1 to 2 carbon atoms;

Y is substituted ethylene joined to the S of S-Z at the α-position, having from 4 to 10 atoms, usually 6–8 atoms, which may be carbon, chalcogen of atomic number 8 to 16 (oxygen and sulfur) and nitrogen and having a β-substituent capable of activating an olefin group for β-thiol addition, usually carbonyl- (including thiocarbonyl-) group; usually having 6 to 8 atoms including 3 to 4 carbon atoms and at least one carbonyl group bound to the olefin wherein nitrogen, if present, is amido; preferably succinimidyl;

n is a number on the average about 2–10 when F is a protein of molecular weight of from about 250,000–1,000,000 daltons, about 3 to 5 when F is a protein of molecular weight of from about 400,000–600,000 daltons;

S-Z is an enzyme having at least one available thiol group.

The preferred compounds of the invention have the following formula:

  (II)

wherein:

F' is ferritin;

m has been defined previously;

R' is a saturated alicyclic linking group having a cycloalkyl portion of from 5 to 7 carbon atoms and an alkylene portion of from 0 to 4 carbon atoms, more usually 1 to 2 carbon atoms; preferably methylenecycloalkyl, more preferably methylenecyclohexyl;

Y' is α-succinimidyl;

n' is on the average about 3 to 4;

S-Z' is β-galactosidase.

For purposes of illustration and not limitation the invention will be described in greater detail employing ferritin as exemplary of a high molecular weight protein and β-galactosidase as exemplary of an enzyme which falls within the purview of the present invention. The present invention is particularly applicable to high molecular weight proteins which are sensitive to a pH below about 6. Ferritin is a protein of molecular weight above about 460,000 daltons. The conjugate will usually consist of a single ferritin molecule covalently bonded on the average to at least about three, and not more than about four, β-galactosidase molecules.

Conjugation of the β-galactosidase molecules to the ferritin is achieved through an inert linking group providing a covalent connection. The term "inert" is used to signify that the linking group will remain substantially unchanged during the binding reactions which take place in the assay. The group will be a bifunctional radical. One of the functionalities will be reactive to the amino groups of ferritin, usually a carbonyl functionality (including nitrogen-imino and thio analogs) for example, a non-oxo-carbonyl (substituted carbonyl derivative) such as oxycarbonyl (carboxy) group, alkoxycarbonyl (ester), carboxycarbonyl (anhydride), and halocarbonyl (halide). The carboxy group can be activated in a variety of ways to react with amino groups to form peptide bonds with amino groups of ferritin, for example, p-nitrophenyl esters or N-oxy succinimide ester. The other functionality is reactive to thiol groups of an enzyme and is usually an activated olefin group, that is, olefin activated for reaction with an available thio group of the enzyme, usually olefin substituted with a functionality which enhances the electro-positive character of the olefin, generally carbonyl-activated olefin, and is stable at a pH of approximately 7.0, such as, for example, N-(4-carboxycyclohexylmethyl)maleimide and maleimidoacetyl. The reaction conditions employed in the formation of the conjugate will normally reflect the particular functionality used in forming the bond. For conjugation of the linking group to the high molecular weight protein, the conditions are conventional, e.g., as disclosed in U.S. Pat. No. 3,817,837 (incorporated herein by reference thereto).

For conjugation of the linking group to the enzyme it is desirable to block any available thiol groups on the ferritin molecule. This will assure that only thiol groups on the enzyme will bind to the functionality on the linking group during formation of the ferritin-enzyme conjugate. As a blocking agent one may use an agent containing a functionality reactive only to thiol groups, such as activated olefin, generally carbonyl-activated olefin, e.g., N-ethyl maleimide, or an α-halogenated amide such as α-haloacetamide.

The reaction mixture during conjugation of the linking group to the enzyme will normally be brought to a pH in the range of about 7 to 10, more usually in the range of about 7 to 9. Various buffers may be used, such as phosphate, carbonate, Tris and the like. An aqueous solvent will normally be used and up to about 40 weight percent of an oxyethylene alcohol or ether having from 1 to 3 oxyethylene units may be present. Particularly useful is carbitol. The temperatures will normally range from about −5° C. to about 40° C., usually from about 0° C. to about 25° C.

The mole ratio of the β-galactosidase in the coupling reaction mixture will be such as to allow introduction, on the average, of about 3 to 4 enzyme molecules per molecule of ferritin. Generally, the molar ratio of β-galactosidase to ferritin is at least about 15:1 or greater.

In preparing the conjugates, it is desirable that the enzyme retain on the average at least 10%, preferably at least about 40%, of its original enzyme activity. Furthermore, at least one epitopic site on the ferritin in the conjugate should be left accessible to a macromolecular receptor. The receptor will be any compound or composition capable of recognizing a particular spatial or polar organization of ferritin (i.e., a determinant or epitopic site) and which has specific binding affinity for ferritin. Illustrative receptors include naturally occurring and synthetic materials such as immunoglobulins and antibodies. The conjugate of the invention, upon the binding of receptor, causes a reduction of at least about 30%, preferably at least about 50%, in the activity of the enzyme. As an optional variation, a second receptor can be introduced with specificity for the first receptor or for the complex formed by the bonding of the first receptor to the conjugate. Use of the second receptor can increase overall enzyme inhibition or provide for the same degree of inhibition using a lesser amount of the first receptor.

As the enzyme one may use any enzyme herein which has at least one available thiol group, the activity of the enzyme being substantially inhibited upon the binding of the ligand of the ligand-enzyme conjugate to a receptor for the ligand. Generally, the enzyme will require a macromolecular substrate with the preferred enzyme being $\beta$-galactosidase.

Any substrate which produces a detectable signal in conjunction with the enzyme employed in the conjugate can be used. This includes both chromogenic and fluorogenic substrates. Macromolecular substrates will be employed. Preferred macromolecular substrates are polysaccharide macromolecular supports to which is attached an enzyme substrate; for example, a galactosidyl ether of nitrophenol or umbelliferone when the enzyme employed in the conjugate is $\beta$-galactosidase. Exemplary substrates in the latter instance are disclosed in Skold, U.S. Pat. No. 4,268,663, issued May 19, 1981, and Madhave et al., *Enzyme*, 25:127–131 (1980). Various other $\beta$-galactoside derivatives, exemplified in the literature, can serve as substrates.

The assay method in general is well known. An extensive description is found in Rubenstein et al., U.S. Pat. No. 3,817,837, issued June 8, 1974, incorporated herein by reference.

Generally, the method for determining the presence of analyte in a sample comprises examining for the effect of the sample containing the analyte on the modulation of enzymatic activity that occurs when a conjugate in accordance with the present invention is contacted with a receptor, when compared to the signal obtained in the absence of analyte. Normally, the method for determining the presence of an analyte such as ferritin in a medium suspected of containing the analyte involves bringing together in an aqueous liquid zone the medium, a conjugate of the analyte and an enzyme in accordance with the present invention, and a receptor having sites common to and capable of binding to the analyte and to the particular conjugate employed, such as an antibody. The receptor is normally at a concentration resulting in reduction of at least 20%, usually about 50% or more, in enzymatic activity of the conjugate when compared to the enzymatic activity of the conjugate in the absence of the medium to be assayed. The effect of the medium on the enzymatic activity of the conjugate is analyzed and may be compared to the effects obtained with samples containing known amounts of analyte. The assays will normally be carried out at moderate temperatures, usually in the range of about 15 to 40° C. The pH of the assay solutions will be in the range of about 7 to 10, usually about 7 to 9. Generally, buffers are included in the assay medium, e.g., (trishydroxymethyl)methylamine salt, carbonate, borate, and phosphate.

Whether oxygen is present or the assay is carried out in an inert atmosphere, will depend on the particular assay. Where oxygen may be an interferant, an inert atmosphere will normally be employed. Normally, hydroxylic media will be employed, particularly aqueous media, since these are the media in which the enzyme is active. However 0 to 40 volume percent of other liquids may also be present as co-solvents, such as alcohols, esters, ketones, amides, etc. The particular choice of the co-solvent will depend on the other reagents present in the medium, the effect on enzyme activity, and any desirable or undesirable interactions with the substrate or products.

As mentioned above, the compounds of the invention provide enhanced signal in the above assay which has heretofore been unattainable. Conjugation of ferritin and $\beta$-galactosidase by means of linking groups closely-related to the above, e.g., maleimidobenzoyl, does not allow for the requisite number of enzyme subunits per ferritin molecule necessary for an enhanced signal.

In carrying out the subject assays, in order to obtain reproducible results, it is desirable that the critical reagents be provided in predetermined ratios for combination in the assay, e.g., in kit form, so as to optimize the sensitivity of the assay. In the assay for ligand, the critical reagents include labeled ligand (conjugate). Besides the desire to have the critical reagents in predetermined proportions, it is frequently desirable that ancillary materials, such as buffer, stabilizers and the like, be included with critical reagents, so that dry powders or concentrates may be diluted to form assay solutions directly, avoiding the necessity of individually weighing the various materials.

In the kit, the reagents will be provided in relative proportions, so as to substantially optimize the sensitivity of the assay to the concentration range of interest. In addition, included with one or both of the reagents may be buffer, inert proteins, such as albumins, stabilizers, such as sodium azide and the like. Desirably, the reagents are provided as dry powders.

The following is offered by way of illustration and not by way of limitation.

EXAMPLES

All temperatures are in centigrade. All parts and percents not otherwise indicated are by weight, except for mixtures of liquids, which are by volume. All solutions are aqueous solutions unless otherwise indicated. The following abbreviations are used:

| | |
|---|---|
| h: | hour; |
| PBS,N$_3$,Mg: | phosphate buffered saline; consists of 10 mM PO$_4$, 150 mM NaCl, 5 mM NaN$_3$ and 1 mM Mg$^{++}$, at pH 7.0; |
| EtOH: | ethanol |
| DTE: | dithioerythritol |
| DMF: | dimethyl formamide |
| NEM: | N—ethyl maleimide |
| EDCI: | ethyl dimethylaminopropyl carbodiimide |
| RSA: | rabbit serum albumin |
| DONPG: | dextran linked o-nitrophenyl-$\beta$-D-galactose (prepared according to U.S. Pat. No. 4,268,663 |
| DUG: | dextran linked umbelliferone $\beta$-galactoside (dextran of 40,000 molecular weight wherein about 14% of its amino groups were modified with umbelliferone galactoside groups |

EXAMPLE I

Preparation of the Conjugated of Ferritin and β-Galactosidase

A. Alkylation of Available Thiol Groups of Ferritin

A solution consisting of pb 600 μg purified human ferritin in 750 μl PBS,N₃,Mg was dialyzed against 0.05M phosphate buffer at pH 7.0. The dialyzed solution was then combined with 10 μl of a 10 mM solution of DTE. The resulting mixture was stirred at room temperature for one hour, then combined with 30 μl of a DMF solution of NEM (10 mg/ml concentration), and stirred an additional thirty minutes at room temperature. The mixture was then dialyzed twice against 0.05M phosphate buffer at pH 7.0. The final mixture was then checked for aggregates by electrophoresis in a 4% polyacrylamide gel containing sodium dodecyl sulfate and β-mercaptoethanol.

B. Conjugation of Ferritin to β-Galactosidase

To 0.5 ml of the final mixture of I A above was added 20 μl of a DMF solution of the N-hydroxysuccinimide ester of N-(4-carboxycyclohexylmethyl) maleimide (10 mg/ml concentration). The resulting mixture was stirred at room temperature for thirty minutes, then dialyzed twice against 0.05M phosphate buffer at pH 7.0. The dialyzed mixture was combined with 7 mg of β-galactosidase dissolved in 0.05M phosphate buffer at pH 7.0 (solution volume 5 ml) and stirred at room temperature for 24 hours. The final mixture was chromatographed on a 2.5×90 cm Biogel A5m(200–400 mesh) column equilibrated with PBS,N₃, Mg. The solution was eluted at 17 ml/h and 86-drop fractions (5 ml each) were collected.

C. Determination of Antibody Loading Curve With Chromogenic Substrate

Based on ability to inhibit enzyme activity by anti-ferritin binding, fractions 36 through 40 above were pooled and used to determine an antibody loading curve.

A series of mixtures was prepared, each consisting of 100 μl rabbit anti-human ferritin (at serial dilutions), 70 μl 1.15×PBS,N₃,Mg containing 0.1% RSA and 30 μl of the conjugate pool. The mixtures were incubated for 2 h at room temperature. To each mixture was added 800 μl of 0.4 mM DONPG in 1.15×PBS, N₃,Mg containing 0.1% RSA. The optical density of each solution at 420 nm was read at 37° at 10 and 40 seconds after the samples were placed in the flow cell. The change in optical density and percent inhibition as compared with mixtures lacking antibodies are listed in Table I, where it is clear that the conjugate will be effective for use in a competitive-type chromogenic immunoassay.

TABLE I

Ferritin β-Galactosidase Conjugates:
Antibody Loading Curve
Measured by Chromogenic Detection

| Inverse of Dilution | ΔOD | Single Antibody % Inhibition |
|---|---|---|
| 1 | 47 | 75 |
| 3 | 57 | 69 |
| 9 | 67 | 64 |
| 27 | 76 | 59 |
| 81 | 88 | 52 |
| 243 | 105 | 43 |
| 729 | 111 | 40 |
| 2,187 | 154 | 17 |
| 6,561 | 169 | 9 |
| 19,683 | 180 | 3 |
| 59,049 | 181 | 2 |
| 177,147 | 186 | 0 |
| 531,441 | 188 | 0 |
| 1,594,323 | | |

EXAMPLE II

Determination of Antibody Loading Curve With Fluorogenic Substrate

Fluorogenic substrate (DUG) was prepared as follows:

Umbelliferone-3-carboxylic acid ethyl ester was prepared according to the procedure of G. Schuman, H. Hansen, *Archiv der Pharmazie*, 271, 490 (1933). Next, a creased, 3-necked, 24/40 round bottomed flask was fitted with an overhead stirrer in the center neck, a nitrogen inlet with stopcock in the left neck, and a stopper in the right neck. HPLC grade CH₃CN (380 ml) was added to the flask followed by the umbelliferone ester from above (18.31 g, 78.2 mmol). The mixture was heated to dissolve all the solid. Acetobromo-α-D-galactose (solid, 39.0 g, 89.7 mmol, Sigma Chemical Co.) was added all at once.

Ag₂O (9.3 g, 80.0 mmol) was then added in spatula portions over a period of 5–10 minutes to the very vigorously stirred solution. When the additions were finished, the mixture was stirred an additional 30 minutes. Stirring was stopped, and the contents were allowed to settle for 2 hours.

The reaction mixture was filtered through a medium frit into a 500-ml suction flask. The filter cake was washed with two 15-ml portions of CH₃CN. The combined filtrates were concentrated to a heavy oil. The oil was taken up in 200 ml of CH₂Cl₂ and was washed in a 500-ml separatory funnel with two 50-ml portions of pH 7.0 sodium phosphate buffer (0.1M phosphate) chilled to 0°, followed by a 25-ml portion of saturated aqueous NaCl. The yellow solution was dried over MgSO₄ for 2 hours. The solution was then filtered and concentrated to a heavy oily foam.

To the oily foam was added 50–100 ml of absolute EtOH. Tne solid which formed was collected on a glass frit and washed with a 10–20-ml portion of EtOH chilled to 0°. The solid was then recrystallized from 225 ml of absolute EtOH to give, after washing with two 10-20-ml portions of EtOH chilled to −15° and drying on the filter and under vacuum, 30.56 g of fine needles. Concentration of the combined EtOH mother liquors (300–350 ml) to 200 ml yielded an additional 1.3 g of pure product.

A total of 31.86 g of tetraacetylgalactosylumbelliferone-3-carboxylic acid, ethyl ester was obtained (72.2%), m.p. 157–158.5°.

The ester tetraacetate from above (28.22 g, 50 mmol, 250 meq of ester) was suspended in 250 ml of absolute EtOH in a 1000-ml round bottom flask under N₂. KOH (56 g of 85%, 850 mmol) was weighed into a 250 ml stoppered Erlenmeyer flask. Water (250 ml of deionized H₂O) was added to the KOH with swirling and cooling (ice bath). When solution was complete and its temperature had cooled to ~10°, the KOH solution was added to the stirring solution of the ester tetraacetate. Three 12-ml portions of H₂O were used to rinse the KOH Erlenmeyer contents into the reaction flask. The reaction flask was covered by aluminum foil and left to stir overnight.

After 16 h the solution was very slightly turbid. Addition of ~10 ml of H₂O caused clarification.

The solution was acidified with 70.8 ml of ice cold concentrated HCl added very slowly with cooling in an ice bath. The solution was concentrated to ~225-250 ml. A white solid precipitated and was collected in a large fritted glass funnel and washed with two portions of 1N HCl (15 ml at 0°) and 2 portions of CH₃CN (30 ml). The solid was recrystallized from ~50 ml of near boiling H₂O and the hot solution was filtered. On cooling to room temperature and then to 4° for 2 days a mass of white needles was obtained. These were collected on a glass fritted funnel, washed with 2×10 ml of ice cold 1N HCl and 2×20 ml of CH₃CN, and air-dried in the funnel to give 15.5 g (77%) of the galactosylumbelliferyl-3-carboxylic acid dihydrate. Concentration and recrystallization of the mother liquor gave an additional 480 mg of product.

Further purification was achieved by recrystallization once or twice from dry, HPLC grade CH₃CN. To 1.5 l of refluxing CH₃CN was added 5 g of the acid dihydrate from above that had been dried under vacuum with heating. The mixture was heated near reflux until all the solid dissolved, usually about 4 minutes. The solution was filtered on a pre-heated Buchner funnel into a preheated 2 l. suction flask. The solution was allowed to cool to room temperature sealed from moisture. The flask was placed in the cold room overnight.

The resultant crystals were collected by filtration, washed with three 25-ml portions of CH₃CN, and placed under high vacuum to dry. This gave 4.7 g (94%) of galactosyl unbelliferone acid as an anhydrous hydroscopic white solid:

nmr: (D₂O) concentration dependent, $\delta$8.7 (1,s,H4), 7.7 (1,d,H5), 7.17 (1 dd, H6) 7.05 (1,dd,H8), 5.27 (1,m,H1'), 3.8–4.35 (6,m,H2'-6')ppm.

uv: $\lambda max = 333$ nm, $\epsilon = 11,200$ (pH 8.75, phosphate buffer).

Anal. (Dihydrate) Calcd for $C_{16}H_{20}O_{12}$: C ,47.53; H, 4.99. Found: C, 47.51; H, 4.90.

Anal. (anhydrous) Calcd for $C_{16}H_{16}O_{10}$: C,52.18; H, 4.38. Found: C, 50.39; H, 4.86 (Calcd for 0.75 eq H₂O: C, 50.44; H, 4.61

Aminodextran was prepared by dissolving dextran T40 (101 g) in 1.25M aqueous sodium chloroacetate (500 ml). A 2.5M aqueous solution of sodium hydroxide (500 ml) was added. The solution was heated at 80°–85° for 3 hr.

The reaction mixture was allowed to cool. Ethanol (1 l.) was added slowly to the stirred reaction mixture. The dextran began to precipitate after 350 ml had been added. Additional ethanol (2 l.) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l.) was then added slowly until a permanent cloudiness appeared in the solution, then more rapidly. The gummy precipitate of the dextran was then allowed to settle out overnight.

Carboxymethylated dextran T40 (as a gum, prepared from 100 g dextran T40) was dissolved in water (250 ml). A solution of N,N'-bis-(3-aminopropyl)piperazine (400 g, 2.0 mole) in hydrochloric acid (680 g of 8.52 mmole/g. 5.80 mole) was added. To the resulting solution was added EDCI (201 g, 1.05 mole) in water (250 ml). The reaction was stored at room temperature for 22 hrs. At the end of this period, ethanol (3 l.) was added. The dextran began to precipitate after 1.5 l. had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted in 1 l and found to be 104 mM in amino groups by assay with trinitrobenzenesulfonic acid. A solution of the aminodextran (1 l of 104 mM, 104 mmole) was treated with $K_2HPO_4$(89 g,0.5 mole) to give a solution buffered at pH 8–8.1.

The galactosyl umbelliferone acid from above (281 mg, 0.763 mmole) was weighed quickly into a pear-shaped flask containing a stir bar, and the flask was stoppered to protect the contents from atmospheric moisture. By means of a 10-ml syringe, 6 ml of DMF was added. The flask was stoppered and the mixture stirred to form a homogeneous suspension. EDCI (139.6 mg, 0.72 mmol) and NHS (87.9 mg, 0.764 mmol) were weighed and added to the stirring suspension. A bright yellow-orange solution resulted in the stoppered flask in two to five minutes. The flask was covered with aluminum foil and allowed to stir 2 h.

The aminodextran from above (53.78 g of solution) was weighed into a 250 ml, 3-necked, round-bottomed flask containing a football stir bar. The solution was brought to a pH of 8.3 (pH meter) by careful addition of concentrated NaOH. The electrode was rinsed into the flask to recover all the aminodextran.

To the vigorously stirring aminodextran solution was added dropwise from a 20 ml syringe the DMF solution of the galactosylumbelliferone acid NHS ester prepared above. The addition took 5–10 minutes. Three 0.5 ml portions of DMF were used to rinse the residual NHS ester from its reaction flask and the addition syringe into the aminodextran solution. The aminodextran flask was then stoppered, covered with aluminum foil, and allowed to stir 3 h.

The solution was then brought to a pH of 5.5 (pH meter) by careful addition of concentrated HCl. After acidification the product was precipitated by slow addition of 170 ml of 95% ethanol to the vigorously stirred solution. Precipitation began after 40 to 60 ml of ethanol had been added. The resultant gum was allowed to settle overnight at 4° in the stoppered flask covered by aluminum foil.

The supernatant was then decanted and discarded. The gum was rinsed with three 20-ml portions of 95% ethanol. The ethanol was drained as thoroughly as possible from the gum. To the crude product was added 10 ml of H₂O. The mixture was stirred and after about 1 h a clear, light brown, viscous liquid resulted. The liquid was transferred to Spectrapor ® 1 dialysis bags. The bags were dialyzed into 4 liters of an aqueous solution containing 0.01M $NaH_2SO_4$ and 0.005M $NaN_3$. Buffer was changed at intervals of 4 to 48 h, and a total of 6 changes were made.

The contents of 3. Buffer was changed at intervals of 4 to 48 h, and a total of 6 changes were made.

The contents of the bags were then centrifuged for 1 h at 16,000 rpm. Tne contents were carefully transferred to new tubes and centrifuged a second time. The clear supernatants were filtered through a 0.22 μm Millipore ® filter. The product was analyzed and characterized, $\lambda_{max} = 342.5$ nm (pH=7.0, 10 mM phosphate buffer), and then stored frozen in aliquots.

A series of mixtures was prepared, each consisting of 100 μl rabbit anti-human ferritin (at serial dilutions) and 100 μl of the pooled conjugate used in Example III above at 1/200 dilution in 1.75×PBS,N₃,Mg containing 0.1% RSA. A second series was prepared further containing 10 μg goat anti-rabbit Ig,N₃,Mg containing 0.1% RSA. A second series was prepared further containing 10 μg goat anti-rabbit IgG per mixture. The mixtures were then incubated at room temperature for 3 hours, after which time 800 μl of 0.2 mM DUG in 1.75×PBS,N₃,Mg containing 0.1% RSA was added. The fluorescence values were read (in fluorunits) at 10 and 40 seconds at 37° and the results are listed in Table II, where it is clear that the conjugate can also be effectively used in a competitive-type fluorogenic assay.

TABLE II

Ferritin β-Galactosidase Conjugates:
Antibody Loading Curve
Measured by Fluorogenic Detection

| Weight of Antibody | Single Antibody | | Double Antibody | |
|---|---|---|---|---|
| | Δ Fluorunits | % Inhibition | Δ Fluorunits | % Inhibition |
| 95 ng | 220.8 | 33 | | |
| 31.7 | 229.8 | 30 | 185.0 | 38 |
| 10.6 | 243.6 | 26 | 176.0 | 41 |
| 3.5 | 263.2 | 20 | 191.4 | 36 |
| 1.2 | 289.6 | 12 | 203.2 | 32 |
| 391 pg | 302.8 | 8 | 221.4 | 26 |
| 130 | 315.6 | 4 | 238.0 | 21 |
| 43.4 | 316.6 | 4 | 248.6 | 17 |
| 14.4 | 319.2 | 3 | 258.8 | 14 |
| 4.8 | 325.4 | 1 | 277.0 | 8 |
| 1.6 | 328.8 | 0 | 292.0 | 2 |

From the above data it can be seen that the conjugate of ferritin and β-galactosidase in accordance with the present invention provides for a significant level of inhibitability in the above immunoassays. Inhibition is enhanced by the use of a double antibody technique. Thus, the above-described conjugates may be used effectively to obtain accurate results in immunoassays for ferritin.

Although the foregoing invention has been described in some detail by way of illustration and example for purposes of clarity of understanding, it will be obvious that certain changes and modifications may be practiced within the scope of the appended claims.

What is claimed is:

1. A compound of the formula:

wherein:
F is a protein of molecular weight of from about 250,000–1,000,000 daltons;
m is 0 or 1;
R is a saturated alicyclic linking group having a cycloalkyl portion of from 5 to 7 carbon atoms and an alkylene portion of from 0 to 4 carbon atoms;
Y is substituted ethylene joined to the S of S-Z at the α-position having from 4 to 10 atoms comprising carbon, chalcogen of atomic number 8 to 16 and nitrogen and having a β-substituent capable of activating an olefin group for β-thiol addition;
n is a number from 2 to about 10;
S-Z is an enzyme with an available thiol group.

2. The compound of claim 1 wherein R is methylenecycloalkyl.

3. The compound of claim 1 wherein said β-substituent is carbonyl.

4. The compound of claim 1 wherein F is a protein of molecular weight of from about 400,000–600,000 daltons and n is from about 3 to 5.

5. The compound of claim 1 wherein F is ferritin and n is 3 or 4.

6. The compound of claim 1 wherein S-Z is β-galactosidase.

7. The compound of claim 1 wherein Y is α-succinimidyl.

8. A compound of the formula:

wherein:
F' is ferritin;
m is 0 or 1;
R' is a saturated alicyclic linking group having a cycloalkyl portion of from 5 to 7 carbon atoms and an alkylene portion of from 1 to 2 carbon atoms;
Y' is α-succinimidyl;
n' is about 3 or 4;
S-Z' is β-galactosidase.

9. The compound of claim 8 wherein R' is methylenecyclohexyl.

10. A method for determining the presence of a high molecular weight protein in a medium suspected of containing the same, which comprises:
contacting -
(a) a medium suspected of containing a high molecular weight protein,
(b) a compound according to claim 1, and
(c) a receptor having sites common to and capable of binding to said high molecular weight protein and to said compound according to claim 1 wherein said receptor is at a concentration resulting in a substantial change in enzymatic activity of said compound, and
analyzing for the effect of said medium on the enzymatic activity of said compound.

11. The method of claim 10 wherein said medium, said compound, and said receptor are contacted in an aqueous liquid zohe.

12. The method of claim 10 wherein the high molecular weight protein is ferritin.

13. An immunoassay kit for analyzing for the presence of a high molecular weight protein in a medium suspected of containing the same, comprising, in predetermined ratios for combination with the medium, a compound according to claim 6 and a receptor having sites common to and capable of binding to said high molecular weight protein wherein said receptor is at a concentration resulting in a substantial change in enzymatic activity of said compound.

14. The immunoassay kit of claim 13 wherein the high molecular weight protein is ferritin.

15. A method for determining the presence of ferritin in a medium suspected of containing ferritin, which comprises:

combining -
(a) a medium suspected of containing a high molecular weight protein,
(b) a compound according to claim 8; and
(c) antibody for ferritin at a concentration resulting in a substantial change in enzymatic activity of said compound, and analyzing for the effect of said medium on the enzymatic activity of said compound.

* * * * *